United States Patent [19]

Baer et al.

[11] 4,334,087

[45] Jun. 8, 1982

[54] PROCESS FOR PREPARING α-KETOCARBOXYLIC ACIDS

[75] Inventors: Ted A. Baer; Jeffrey N. Labovitz, both of Palo Alto, Calif.

[73] Assignee: Zoecon Corporation, Palo Alto, Calif.

[21] Appl. No.: 186,360

[22] Filed: Sep. 11, 1980

[51] Int. Cl.³ .................... C07C 59/76; C07C 59/80; C07C 59/86; C07C 62/38

[52] U.S. Cl. .................... 562/459; 260/413; 260/465 F; 260/465.6; 546/340; 546/341; 549/66; 562/426; 562/433; 562/440; 562/464; 562/507; 562/508; 562/577; 549/488

[58] Field of Search ............ 562/549, 577, 426, 433, 562/440, 464, 507, 508, 577; 260/347.3, 413, 465 F; 546/340, 341; 549/66

[56] References Cited

U.S. PATENT DOCUMENTS

| | | | |
|---|---|---|---|
| 3,254,109 | 5/1966 | Hartle | 562/459 |
| 3,897,467 | 7/1975 | Anatol | 562/459 |
| 4,234,739 | 11/1980 | Photis | 562/459 |

OTHER PUBLICATIONS

Davies, J. H. et al., J. Chem. Soc. (C), pp. 431–435, 1968.

*Primary Examiner*—Paul J. Killos
*Attorney, Agent, or Firm*—Donald W. Erickson; Jacqueline S. Larson; Thomas T. Gordon

[57] ABSTRACT

A novel process for the manufacture of α-ketocarboxylic acids which comprises the reaction of oximinohalide with cyanide ion to form oximinonitrile which is reacted with hydroxide ion to form oximinoacid and hydrolysis thereof to the α-ketoacid.

12 Claims, No Drawings

PROCESS FOR PREPARING α-KETOCARBOXYLIC ACIDS

This invention relates to a novel process for the manufacture of α-ketocarboxylic acids.

α-Ketoacids are useful intermediates in the manufacture of, for example, pharmaceutical and agricultural chemicals, most notably, α-amino acids.

The process of the present invention is advantageous in that it utilizes inexpensive, readily available starting materials, thereby providing means for economically preparing α-ketocarboxylic acids, which in turn allows inexpensive preparation of α-amino acids and other chemicals. An additional advantage is that the process of the present invention gives a high yield of the α-ketoacids. A further advantage is that the process can be carried out in a single reaction vessel.

The process of the present invention can be outlined as follows.

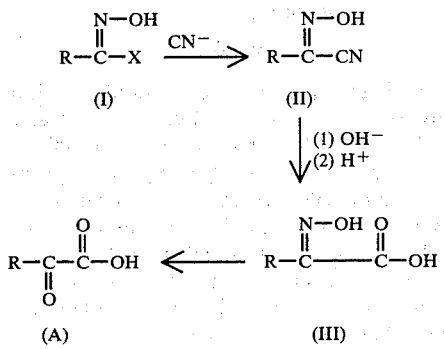

In the practice of the above outlined process, an oximinohalide of formula (I) is reacted with at least one equivalent of cyanide ion to form an oximinonitrile of formula (II). The reaction can be carried out in aqueous medium and using, for example, sodium cyanide or potassium cyanide as the source of cyanide ion. The reaction is exothermic and usually is run by starting the reaction at low temperature of the order of about −5° to 10° and then allowing the reaction temperature to warm to about room temperature. The reaction is usually complete within about 0.5 to 2.0 hours. The nitrile (II) is soluble in organic solvents and can be isolated by extraction, if desired, or used in the next step of the process without isolation.

The oximinonitrile (II) is reacted with at least two equivalents of hydroxide ion to form, after acidification of the reaction medium, the oximinoacid (III). The reaction can be carried out in aqueous medium and using, for example, sodium hydroxide or potassium hydroxide as the source of hydroxide ion. The reaction is conducted in an aqueous medium with heating such as heating to the reflux temperature of the reaction mixture. The hydroxide ion can be added in aqueous solution to the reaction product of the previous step without isolation of the oximinonitrile. The reaction is usually complete within about one to three hours. Following reaction of the oximinonitrile (II) with hydroxide ion, the reaction medium is acidified in the customary manner of neutralizing acid salt to the free acid such as by addition of dilute sulfuric acid, HCl, or the like.

The oximinocarboxylic acid (III) is then hydrolyzed to form the α-keto acid (A) which is then recovered from the reaction medium. The hydrolysis can be carried out by the treatment of the oximinoacid (III) in aqueous medium with $H_2SO_4$, HCl or the like in the presence of formaldehyde.

In the above outlined process, X represents bromo, chloro or iodo and R represents hydrogen or an organo group. The selection of the organo group R is not critical except as governed by the choice or selection of α-ketoacid it is desired to manufacture by the process of the present invention. The organo group can be an aliphatic group, a heteroaliphatic group, a cycloaliphatic group, an aryl group, an aralkyl group, or a heterocyclic group. The organo group can be substituted with one or more substituents such as hydroxy, mercapto, nitro, fluoro, chloro, bromo, iodo, amino and hydrocarboxy such as alkoxy. The term "aliphatic group" means branched or straight chain, alkyl of 1 to 22 carbon atoms, alkenyl of 2 to 22 carbon atoms and alkynyl of 2 to 22 carbon atoms. The term "heteroaliphatic group" means oxa-alkyl of 2 to 22 carbon atoms, and thia-alkyl of 2 to 22 carbon atoms. The term "cycloaliphatic group" means cycloalkyl of 3 to 8 carbon atoms, cycloalkyl of 4 to 8 carbon atoms, and cycloalkenyl of 4 to 8 carbon atoms. The term "aryl group" means aryl of 6 to 12 carbon atoms. The term "aralkyl group" means aralkyl of 7 to 12 carbon atoms. The term "heterocyclic group" means heterocyclic of 3 to 10 carbon atoms having 1 or 2 hetero atoms selected from oxygen, sulfur and nitrogen. Whenever any of the foregoing terms is modified by the term "lower", the maximum number of carbon atoms is fourteen.

The oximinohalides of formula (I) can be prepared by the reaction of an aldehyde with hydroxylamine followed by halogenation and other methods. See H. Ulrich, *The Chemistry of Imidoyl Halides*, Plenum Press, New York, p. 157 (1968) and J. H. Davies et al., J. Chem. Soc. (C), p. 431 (1968). Examples of oximinohalides of formula (I) include, isopropylhydroxamoyl chloride, phenylhydroxamoyl chloride, 2-propenylhydroxamoyl chloride, cyclopropylhydroxamoyl chloride, cyclopropanemethylhydroxamoyl chloride, 4-hydroxybenzylhydroxamoyl chloride, ethylhydroxamoyl chloride, hydroxymethylhydroxamoyl chloride, mercaptomethylhydroxamoyl chloride, 2-methylpropanylhydroxamoyl, chloride, 2-methylbutanylhydroxamoyl chloride, acethydroxamoyl chloride (methylhydroxamoyl chloride), 4-phenylbenzhydroxamoyl chloride, trimethylacethydroxamoyl chloride, benzhydroxamoyl chloride, trifluoroacethydroxamoyl bromide, 2-methoxybenzhydroxamoyl chloride, diethylacethydroxamoyl chloride, 4-methylphenhydroxamoyl chloride, 2-pyridhydroxamoyl chloride, 2-nitrophenhydroxamoyl chloride, 2,4,6-trimethylphenhydroxamoyl chloride, 4-chlorophenhydroxamoyl chloride, 3-pyridhydroxamoyl chloride, α-furfurhydroxamoyl chloride, thiofurhydroxamoyl chloride, methylthiomethylacethydroxamoyl chloride, and 2-hydroxypropanhydroxamoyl chloride.

The present invention provides an economical process for the manufacture of α-ketocarboxylic acids, salts and esters and α-aminoacids which are useful in, e.g., the pharmaceutical and agricultural industries as described, for example, in U.S. Pat. Nos. 4,076,745 and 4,122,116 and Offenlegungsschrifts 26 14 241, 27 08 185 and 189, 27 34 207 and 28 25 565.

The following examples are provided to illustrate the practice of the present invention. RT means room temperature. Temperature is given in degrees centigrade.

EXAMPLE 1

To a solution of 13.9 g (200 mmol) of $NH_2OH \cdot HCl$ in water at about 10°–20° is added 16.0 g (200 mmol) of 50% sodium hydroxide. To the resulting solution is added 14.4 g (200 mmol) of isobutyraldehyde. This mixture is stirred overnight at room temperature and is then cooled to 5° (in a −10° to −20° dry ice bath). To this is added chlorine gas, at a rate such that the reaction mixture temperature is maintained at ~5°. After chlorine uptake has ceased, stirring is discontinued and the acidic aqueous layer is withdrawn. An aqueous solution of 10.4 g (210 mmol) of sodium cyanide is added, with stirring, to the organic layer, and the mixture is allowed to stir at RT for about two hours. It is then extracted into ether, washed with water and with brine, dried over sodium sulfate, filtered and stripped. The reaction product is purified by distillation to yield 2-oximino-3-methylbutyronitrile, b.p.=105°/15 mm.

EXAMPLE 2

A solution of 3.36 g of 2-oximino-3-methylbutyronitrile, 7 ml of 50% NaOH and 3 ml of water is refluxed under a slow stream of nitrogen until cessation of ammonia evolution. This is allowed to cool to RT. The mixture is then diluted with water and washed with ether to remove the neutrals. The aqueous layer is acidified (HCl) and extracted into ether to give 2-oximino-3-methylbutanoic acid, m.p.=153° (dec).

EXAMPLE 3

A solution of 5.24 g (40 mmol) of 2-oximino-3-methylbutanoic acid, 21 ml of 37% aqueous formaldehyde and 2 ml of conc. hydrochloric acid is stirred overnight at RT. The solution is then diluted with two volumes of water and extracted with ether (2X). The ether extracts are combined, washed with brine, dried over magnesium sulfate, filtered and stripped to yield 2-oxo-3-methylbutanoic acid, b.p.=78°/15 mm.

EXAMPLE 4

To 9.07 g (75 mmol) of benzaldoxime in 25 ml of carbon tetrachloride is added dropwise, at 5°, a solution of 45 ml of carbon tetrachloride saturated with 5.6 g (79 mmol) of chlorine gas. The mixture is stirred for 1 hour in an ice bath and then excess HCl is removed by vacuum. A saturated solution of 7.35 g (150 mmol) of sodium cyanide in water is added dropwise, at 0°. The mixture is stirred for 2 hours as it is allowed to warm to RT. An excess of aqueous sodium hydroxide is added and then the carbon tetrachloride layer is discarded. The aqueous layer is acidified and filtered, and the resulting solid is washed with water and dried to give α-oximinophenylacetonitrile, m.p.=120°–125°.

The benzaldoxime is made by reacting benzaldehyde with $NH_2OH$, following the method of Example 1.

EXAMPLE 5

4.38 Grams (30 mmol) of α-oximinophenylacetonitrile is dissolved in a solution of 7.2 g (90 mmol) of 50% NaOH and 5 ml of water. The mixture is refluxed for about 2 hours, then is extracted with ether. The aqueous phase is acidified, extracted with ether/ethyl acetate, washed with water and brine, dried over sodium sulfate and stripped, yielding α-oximinophenylacetic acid, m.p.=127° (dec).

EXAMPLE 6

3 Grams of α-oximinophenylacetic acid is dissolved in 9 ml of 37% formaldehyde containing a few drops of sulfuric acid. This is stirred overnight at RT, extracted with 3:1 ether:hexane, washed with brine, dried over sodium sulfate, stripped and distilled to yield the final product α-oxophenylacetic acid, b.p.=138°–141°/3.3 mm.

EXAMPLE 7

Following the method of Example 1, each of 2-butenal and 3-butenal is treated with $NH_2OH$, followed by chlorine and then sodium cyanide to give 2-oximino-3-pentenylnitrile and 2-oximino-4-pentenylnitrile, respectively. Each of these two oximinonitriles is reacted with sodium hydroxide following Example 2, to give, respectively, 2-oximino-3-pentenoic acid and 2-oximino-4-pentenoic acid, each of which is then treated with conc. hydrochloric acid and formaldehyde as in Example 3 to yield, respectively, 2-oxo-3-pentenoic acid and 2-oxo-4-pentenoic acid.

In the same manner, the compound α-oximinocyclopropylpropanoic acid is made from the starting compound cyclopropylethanal.

EXAMPLE 8

Following the procedure of Example 1 or Example 4, 2-(4-hydroxyphenyl)acetaldehyde is treated with $NH_2OH$, followed by chlorine and then sodium cyanide to give 2-oximino-3-(4-hydroxyphenyl)propylnitrile. This oximinonitrile is reacted with sodium hydroxide as in Example 2 or 5, yielding 2-oximino-3-(4-hydroxyphenyl)propanoic acid, which is in turn reacted with hydrochloric or sulfuric acid and formaldehyde as in Example 3 or 6 to give the final product, 2-oxo-3-(4-hydroxyphenyl)propanoic acid.

EXAMPLE 9

To 1.60 g of 2-oximino-3-methylbutanoic acid is added 0.20 g of 10% palladium on carbon, 13 ml of methanol and 13 ml of ethanol. This mixture is stirred under 50 psi hydrogen pressure overnight at RT, followed by dilution with water, filtration and stripping to yield the amino acid valine.

In the same manner, 2-oximino-3-(4-hydroxyphenyl)-propanoic acid is reacted with 10% palladium on carbon, methanol and ethanol to give the amino acid tyrosine.

EXAMPLE 10

To a solution of 0.50 mole of $NH_2OH \cdot HCl$ in water is added 0.50 mole of sodium hydroxide, followed by addition of 0.50 mole of isobutyraldehyde. This mixture is stirred at RT for from about 2 hours to overnight. Chlorine gas is added to the mixture at −5° to +15° until there is no more uptake of the gas—about 1 to 2 hours. The aqueous brine layer is removed and, at 0°–10°, 0.57 mole of sodium cyanide solution is added, followed by stirring for 2 hours at RT. To the mixture is added 1.25 moles of sodium hydroxide, after which the mixture is washed with ether to remove neutrals. Under a slow stream of nitrogen, the mixture is heated at reflux for 7 hours and then allowed to cool to RT. It is again washed with ether to remove neutrals. The remaining aqueous solution is acidified and to it is added 75 ml of 37% formaldehyde, stirring until all solid has dissolved (a few minutes). The mixture is allowed to stand at RT for about 3 hours, after which it is extracted with ether (3X), back-washed with 50:50 water: brine, dried and distilled, giving the final product, 2-oxo-3-methylbutanoic acid.

EXAMPLE 11

Acethydroxamoyl chloride is converted into 2-oximino-ethanonitrile, using the process of Example 1, which is reacted with aqueous NaOH to form 2-oximinopropanoic acid using the process of Example 2. Following the procedure of Example 9, 2-oximinopropanoic acid is converted into α-alanine.

Hydrolysis of 2-oximinopropanoic acid using the procedure of Example 3 yields 2-oxopropanoic acid.

Methylthiomethylacethydroxamoyl chloride is converted into 2-oximino-4-methylthiobutanoic acid using the process of Examples 1 and 2. Following the procedure of Example 3, 2-oxo-4-methylthiobutanoic acid is prepared. Following the procedure of Example 9, methionine is prepared from 2-oximino-4-methylthiobutanoic acid.

What is claimed is:

1. A process for the manufacture of an α-ketocarboxylic acid of formula (A)

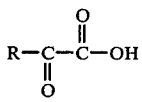

which comprises the steps of:

(a) reacting an oximinohalide of formula (I)

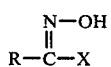

with at least one equivalent of a member selected from the group consisting of sodium cyanide, potassium cyanide and mixtures thereof to form an oximinonitrile of formula (II)

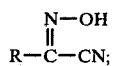

(b) reacting an oximinonitrile of formula (II) with at least two equivalents of hydroxide ion to form an oximinoacid of formula (III)

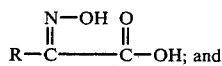

(c) hydrolysis of said oximinoacid in an aqueous medium to form said α-ketocarboxylic acid and recovering the α-ketocarboxylic acid from the medium, wherein X is chloro, bromo or iodo and R is hydrogen or an organo group selected from the unsubstituted and substituted members of the group consisting of alkyl having from 1 to 22 carbon atoms, alkenyl having from 2 to 22 carbon atoms, alkynyl having from 2 to 22 carbon atoms, oxa-alkyl having from 2 to 22 carbon atoms, thia-alkyl having from 2 to 22 carbon atoms, cycloalkyl having from 3 to 8 carbon atoms, cycloalkalkyl having from 4 to 8 carbon atoms, cycloalkenyl having from 4 to 8 carbon atoms, aryl having from 6 to 12 carbon atoms, aralkyl having from 7 to 12 carbon atoms, and heterocyclic having from 3 to 10 carbon atoms and having 1 or 2 hetero atoms selected from oxygen, sulfur, and nitrogen, the substituted members of the group being substituted by at least one substituent from the group consisting of hydroxy, mercapto, nitro, fluoro, chloro, bromo, iodo, amino and hydrocarboxy.

2. The process according to claim 1 wherein X is bromo or chloro, the oximinonitrile is formed by the reaction of the oximinohalide with cyanide ion derived from sodium cyanide or potassium cyanide in an aqueous medium, and the oximinoacid is formed by the reaction of oximinonitrile with hydroxide ion derived from sodium hydroxide or potassium hydroxide in an aqueous medium.

3. The process according to claim 2 wherein the reaction of step (a) is conducted at a temperature of from about 0° to room temperature and the reaction of step (b) is conducted at a temperature of from about 30° to the reflux temperature.

4. The process according to claim 3 wherein R is an alkyl group.

5. The process according to claim 3 wherein R is an alkyl group of 1 to 14 carbon atoms.

6. The process according to claim 3 wherein R is lower alkyl of 1 to 4 carbon atoms.

7. The process according to claim 6 wherein R is isopropyl.

8. The process according to claim 6 wherein X is chloro, the reaction of step (a) is carried out at about room temperature and the reaction of step (b) is carried out at the reflux temperature.

9. The process according to claim 3 wherein R is a phenyl group.

10. The process according to claim 9 wherein X is chloro.

11. The process according to claim 4 wherein X is chloro.

12. The process according to claim 5 wherein X is chloro.

* * * * *